United States Patent [19]
Westdyk

[11] Patent Number: 5,360,337
[45] Date of Patent: Nov. 1, 1994

[54] DENTAL ARTICULATOR

[76] Inventor: Alan M. Westdyk, 749 Kendrew Street, Wingate Park, Transvaal Province, South Africa

[21] Appl. No.: 96,471

[22] Filed: Jul. 22, 1993

[30] Foreign Application Priority Data

Jul. 27, 1992 [ZA] South Africa ............... 92/5630
Apr. 5, 1993 [ZA] South Africa ............... 93/2463

[51] Int. Cl.$^5$ ............................................. A61C 11/00
[52] U.S. Cl. ............................................ 433/64; 433/61; 433/34; 433/57; 433/54
[58] Field of Search .................. 433/54, 58, 60, 64, 433/177, 66, 34, 61, 57

[56] References Cited

U.S. PATENT DOCUMENTS

| | | | |
|---|---|---|---|
| 4,207,677 | 6/1980 | Lampert | 433/60 |
| 4,382,787 | 5/1983 | Huffman | 433/64 |
| 4,449,930 | 5/1984 | Huffman | 433/64 |
| 4,533,323 | 8/1985 | Huffman | 433/60 |
| 4,547,156 | 10/1985 | Hader | 433/177 X |
| 4,548,581 | 10/1985 | Huffman | 433/64 |
| 4,786,253 | 11/1988 | Morais | 433/60 |
| 4,865,544 | 9/1989 | Scruggs | 433/64 |
| 4,946,388 | 8/1990 | Bolton | 433/56 |
| 5,007,829 | 4/1991 | Farrell | 433/64 X |
| 5,221,203 | 6/1993 | Callne | 433/60 X |

FOREIGN PATENT DOCUMENTS 572850 11/1958 Belgium .

Primary Examiner—Gene Mancene
Assistant Examiner—Nicholas D. Lucchesi
Attorney, Agent, or Firm—James Ray & Associates

[57] ABSTRACT

An articulator for a dental model consisting of two dental casts, includes two connecting members 16 for partial embedding in a settable material, a pair of connectors 14 and a hinge 12 consisting of two hinge elements 22. Each connecting member 16 forms one part of a spigot and socket joint and each pair of connectors 14 forms a second part of a spigot and socket joint. Each pair of connectors 14 has an interlocking formation for interlocking engagement with one of the hinge elements 22. The hinge elements 22 are pivotally linked and each has an interlocking formation complementary to the interlocking formations of the connectors 14.

15 Claims, 6 Drawing Sheets

DENTAL ARTICULATOR

FIELD OF THE INVENTION

This invention relates to an articulator for a dental model. It relates in particular to an articulator for a dental model comprising two dental casts.

SUMMARY OF THE INVENTION

According to the invention there is provided an articulator for a dental model comprising two dental casts, the articulator comprising a pair of connecting members for partial embedding in a settable material, each connecting member comprising one part of a spigot and socket joint, a pair of connectors each comprising a second part of a spigot and socket joint, and each having an interlocking formation for interlocking engagement with a hinge element, and a hinge comprising two of the hinge elements pivotally linked, each having an interlocking formation complementary to the interlocking formation of the connectors.

The spigot part of the spigot and socket joint may be of spherical shape.

Each connecting member may include a part of spherical shape of the spigot and socket joint. The spherical part may be bifurcated or split so that it comprises two hemispheres spaced from one another and defining a groove between them. The bifurcated hemispheres may each be mounted on a stalk. The connecting member may be of a resilient or elastically deformable material such as a synthetic plastics material so that the hemispheres may be resiliently or elastically displaceable away from and towards each other. The stalk may be integral with an engagement formation for engagement with a mould as hereinafter described.

The connecting member may be symmetrical in shape having a mirror plane symmetry passing through it so that one side of the connecting member comprising the spherical part, the stalk and a portion of the engagement formation is the mirror image of the other side. The connecting member may thus be provided with two spherical parts, one of which, in use, is embedded in the settable material of a mould. The connecting member may, instead, be provided with any suitable spigot, lug, projection or the like for embedding in the settable material.

The engagement formation may be in the form of a plug of planar shape which, in use, plugs an opening in a mould for the dental cast. The engagement formation may further comprise at least one ridge or flange for engagement with at least one corresponding groove in the sides of the opening in the mould as hereinafter described.

The flange may have a tapering peripheral surface and may have a thickness such that the broadest part of the flange projects into the mould to form a ridge which diverges into the mould.

Each connector may include the socket part of a spigot and socket joint. The socket part may also be of a resilient or elastically deformable material such as a synthetic plastics material and may be generally hemispherical in shape. It may be provided with at least one slit so that the hemispherical socket may be opened by elastic deformability or resilience of the bifurcated spherical parts and the sockets. The spherical parts may, instead, be loosely received in the sockets with little friction between them.

The bifurcation of the spherical part and the slits in the sockets also advantageously results in a larger surface area for receiving an adhesive substance, and allowing the adhesive substance to spread as is described in further detail below.

The interlocking formations of the connectors and hinge elements may be of spigot and socket configuration. For example each connector may comprise the spigot portion and each hinge element may comprise the socket portion. Alternatively, each connector may comprise the socket portion and each hinge element the spigot portion.

Each spigot portion may further be provided with at least one raised engagement or guide formation, such as a ridge or spline, for engagement with a complementary recessed engagement or guide formation such as a groove or channel or spline in each socket portion. Preferably each spigot portion may have a cross-shaped cross sectional profile and each socket portion may have a complementary cross-shaped cross sectional profile. Thus, engagement of the spigot with the socket by inserting the one into the other will interlock the complementary profiles of the spigot and the socket so that rotation of the spigot in the socket is resisted.

The hinge elements may be connected together by a joint of flexible material. The hinge elements and the joint may be integral, the hinge comprising a single body of a flexible material, with the hinge elements being thicker than the flexible joint so that the hinge elements are pivotable about the joint.

Each hinge element may further be provided with reinforcing formations, for example in the form of ridges or ribs to reduce flexibility of the hinge element and enhance its rigidity. Each hinge element may be generally triangular in shape, with the joint of flexible material being located along one of the sides of the triangular shape and the socket portion of the spigot and socket interlocking formations being located on an apex of the triangular shape opposite to the side on which the joint is located.

The hinge and the connectors may be of different synthetic plastics material so that an adhesive will not readily form a bond between them. The hinge may, for example, be of polypropylene and the connectors may be of glass filled nylon. Thus, if an adhesive substance accidentally contaminates the spigot portion of the connector or the socket portion of the hinge, adhesion of the one to the other will be hindered or prevented.

The hinge may include a stay to limit the pivotal movement of the hinge elements with respect to one another. The stay may comprise a screw-threaded pin which can screw into a hole provided in one of the hinge elements and which can abut the other hinge element to thereby limit the pivotal movement of the hinge elements with respect to one another. The stay may alternatively have small nodules which can be ratcheted into the hole provided in one of the hinge elements and which can abut the other hinge element to thereby limit the pivotal movement of the hinge element with respect to one another.

The hole may be elongate in the form of a slot and may have a ridge with which the screw threads of the pin and/or the nodules can co-operate.

The pin may have a gripping formation in the form of a flattened region to facilitate gripping and turning of the pin in the hole.

According to another aspect of the invention there is provided a mould defining a moulding cavity for receiving a settable material for making a dental cast for use with an articulator for a dental model in accordance with the invention.

The mould may be substantially triangular in shape, simulating the shape of a person's jaw and may be open having a floor and side walls defining the moulding cavity into which the settable material may be poured, and may be provided with an opening for receiving an engagement formation as described above. The opening may have sides which are provided with at least one recess or groove for receiving at least one ridge or flange of the engagement formation.

The mould may be of a flexible material which is readily deformable to aid removal of the dental cast after it has set. It may further be provided with bevelled edges to aid removal of the cast after it has set.

According to another aspect of the invention there is provided an articulator kit comprising an articulator and a mould both in accordance with the invention According to another aspect of the invention there is provided a connecting member for an articulator in accordance with the invention.

According to another aspect of the invention there is provided a connector for an articulator in accordance with the invention.

According to another aspect of the invention there is provided a hinge for an articulator in accordance with the invention.

According to another aspect of the invention there is provided a method of assembling a dental articulator, the method including the steps of locating a connecting member in an opening in a mould defining a moulding cavity for a dental cast so that a portion of the connecting member projects from the mould and a portion projects into the moulding cavity; and pouring a settable material into the mould and allowing the settable material to flow around the portion of the connecting member projecting into the moulding cavity and to set thereby forming a dental cast with the connecting member embedded in and projecting from the cast.

The connecting member and the mould may be as hereinbefore described.

The method may include the additional steps of attaching a pair of connectors and a hinge, both as hereinbefore described, to the connecting members of a pair of dental casts.

BRIEF DESCRIPTION OF THE DRAWINGS

The invention is now described with reference to the accompanying drawings in which.

Figure 1:
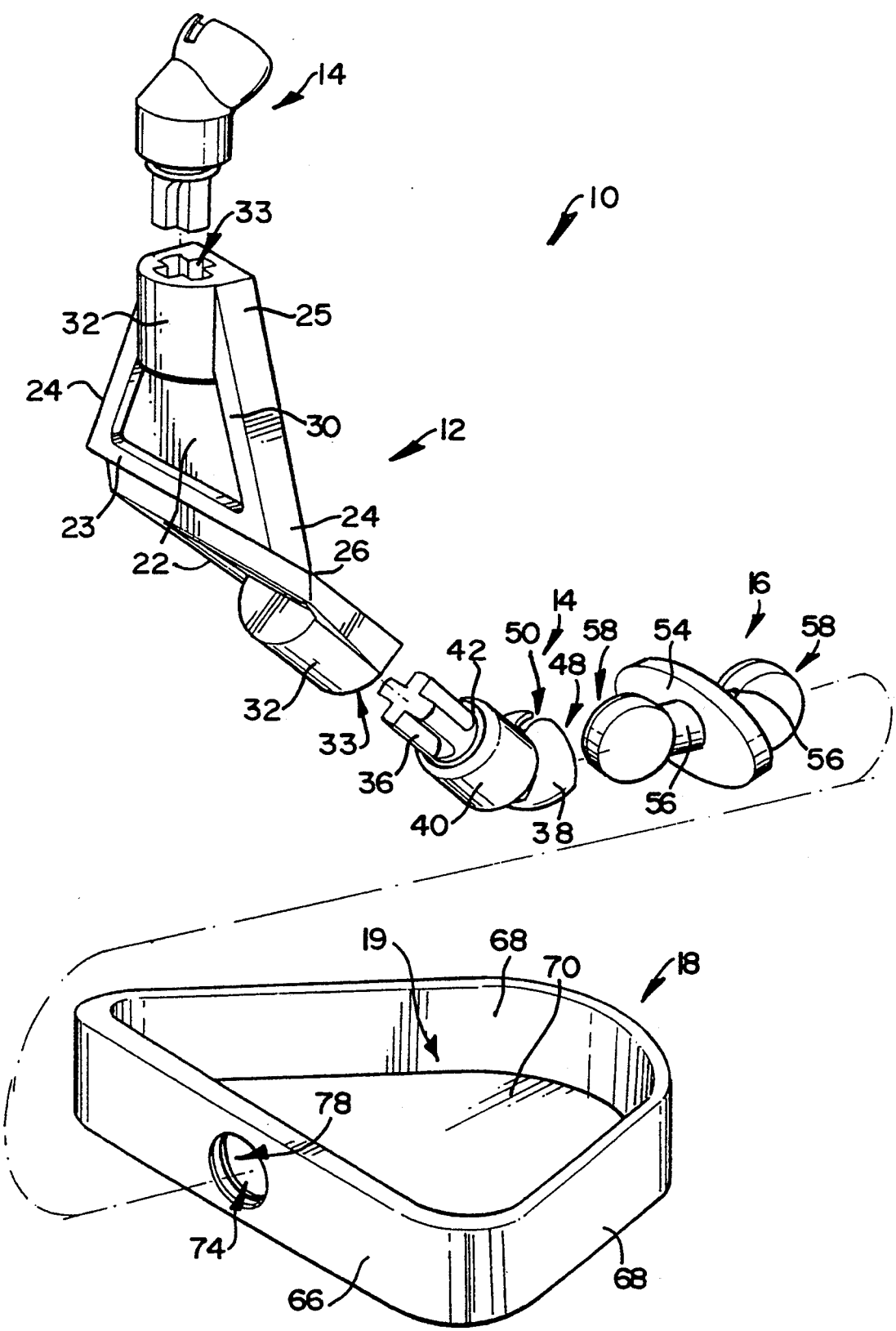
FIG. 1 is an exploded view of an articulator in accordance with the invention.

BRIEF DESCRIPTION OF THE PRESENTLY PREFERRED AND ALTERNATIVE EMBODIMENTS OF THE INVENTION

In the drawings reference numeral 10 generally indicates a part of an articulator kit in accordance with the invention. The kit comprises a hinge generally indicated by reference numeral 12, a pair of connectors, each generally indicated by reference numeral 14, a pair of connecting members each generally indicated by reference numeral 16, and a pair of moulds each generally indicated by reference numeral 18. The second connecting member 16 and the second mould 18 have been omitted from the drawings.

The hinge 12 comprises two generally isosceles triangular-shaped hinge elements 22, each having a base 23, two sides 24 of equal length, and an apex 25 opposite the base 23. Each hinge element 22 is of a flexible material and the elements are connected to one another by a thin flexible joint 26 comprising a narrow web of the same material. In a particular embodiment of the invention the flexible material is polypropylene. The elements 22 are thus pivotable with respect to one another and comprise two halves of the hinge 12. The joint 26 extends along the base 23 of each of the elements 22. A raised ridge 30 extends along all three sides of the triangular shaped hinge element 22 to provide rigidity to the element.

Figure 4:
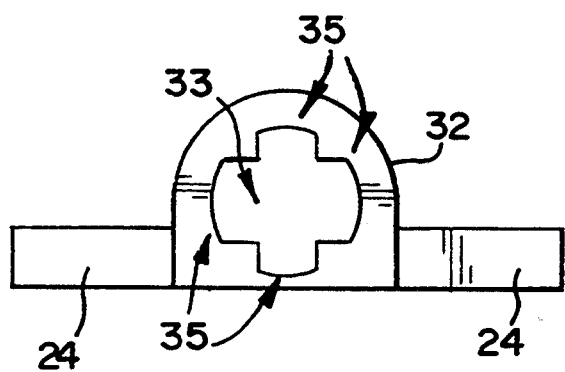
FIG. 4 is an end view, on an enlarged scale, of the hinge socket of the articulator shown in FIG. 1.

A cylindrical-shaped socket 32 having a cylindrical cavity 33 is provided at the apex 25 of the triangular-shaped element 22. The cavity 33 is provided with four symmetrically located inner grooves 35 (shown in FIG. 4) so that it has an internal cross-shaped cross-sectional profile as is described in further detail below.

Figure 2:
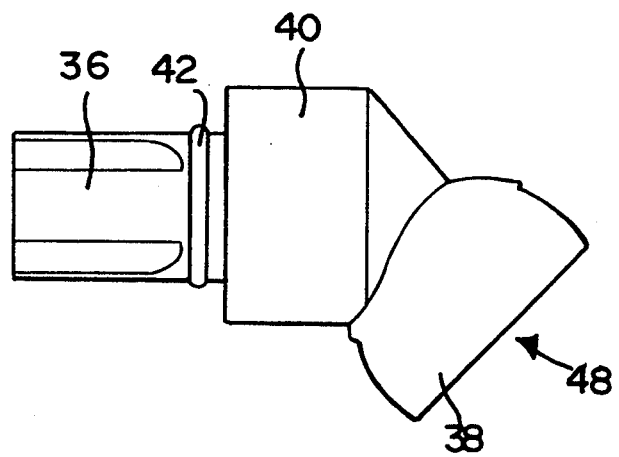
FIG. 2 is a side view, on an enlarged scale, of the connector of the articulator shown in FIG. 1.
Figure 3:
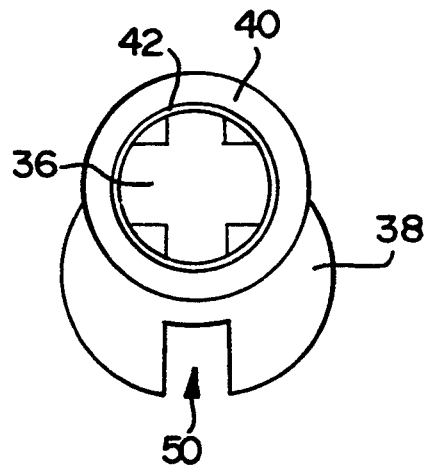
FIG. 3 is a front view, on an enlarged scale, of the connector of the articulator shown in FIG. 1.

The connector 14 comprises a spigot 36 and a part-spherical socket 38 both mounted on a cylindrical base 40 as can be seen in FIG. 2.

The spigot 36 also has a cross-shaped cross-sectional profile for most of its length and has an annular ridge 42 located near to the base 40. The cavity 33 of the cylindrical socket 32, which has a complementary cross-shaped cross-sectional inner profile as mentioned above, also has an annular groove (not shown) located near the rear of the cavity 33 complementary to the annular ridge 42 so that the spigot 36 may be snugly received in the cylindrical socket 30, their cross-shaped cross-sectional profiles engaging with one another and the ridge 42 nesting in the groove.

The part-spherical socket 38 comprises a hollow hemisphere having a cavity 48, and is provided with a pair of slits 50 located on opposite sides of the socket 38. In another configuration (not shown) the socket 38 may be cylindrical instead of part-spherical.

The connector 14 is of a flexible material and is elastically deformable as is described in more detail below. In a particular embodiment of the invention, when the hinge element 22 is of polypropylene, the connector 14 is of glass filled nylon. The spigot 36 and the cylindrical base 40 are co-axial as can be seen in FIG. 2, while the cavity 48 of the socket 38 is directed away from the axis of the spigot 36 and the base 40, the socket 38 being directed at an angle of about 45° with respect to the spigot 36 as can be seen in FIG. 2. The connector 14 is thus an angled connector.

The connecting member 16 comprises a planar oval engagement formation in the form of a plug 54, as is described in further detail below, with connecting formations in the form of a pair of cylindrical stalks 56 projecting symmetrically from opposite sides of the plug 54. Spigot formations in the form of bifurcated spheres 58 each comprising two hemispheres separated by a groove 59 are mounted at the ends of the stalks 56. In another configuration (not shown) the spigot formations 58 may be of cylindrical shape instead of spherical shape. The connecting member 16 is also of a flexible material, which is elastically deformable, so that the two hemispheres of the spheres 58 are elastically displaceable relative to one another. The groove 59 facilitates such displacement. In a particular embodiment of the invention, the connecting member 16 is of glass filled nylon.

In this embodiment of the invention the bifurcated spheres 58 are received with a friction fit in the sockets 38 so that after insertion of the spheres 58 into the sockets 38 as is described in further detail below, the spheres 58 are loosely held in a particular orientation by said friction fit. In another embodiment of the invention the spheres 58 are received in the sockets 38 with little frictional resistance to movement of said spheres. In this embodiment of the invention the spheres are immobilized for the first time by the adhesive as described in further detail below.

The mould 18 is in the shape of an isosceles triangle having rounded apices and defines a moulding cavity 19. The mould 18 has a base wall 66 corresponding to the base of the triangle, side walls 68 corresponding to the sides of the triangle, and a floor 70. The sides 66, 68 and the floor 70 define a cavity for receiving a settable material.

An oval-shaped opening 74 complementary to the oval plug 54 is provided approximately in the middle of the base wall 66 of the mould 18. The side wall of the opening 74 is provided with a groove 78 for receiving the edges of the plug 54 as is described in further detail below.

Figure 5:
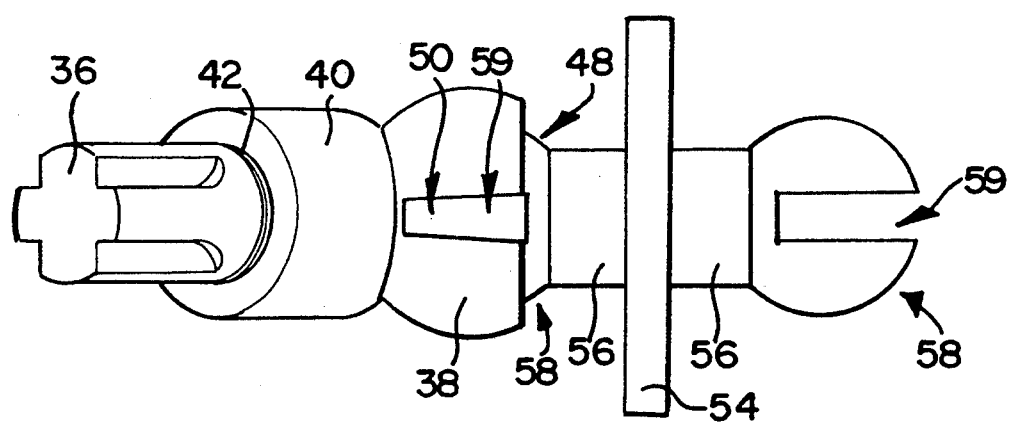
FIG. 5 is a plan view, on an enlarged scale, of the connector and connecting members of the articulator shown in FIG. 1 connected together.

In use, the connecting member 16 is inserted into the opening 74 so that the bifurcated sphere 58 on the stalk 56 projects into the moulding cavity 19 and the edges of the plug 54 are received in the grooves 78 of the opening 74 as can be seen in FIG. 5. The connecting member can be inserted into and removed from the opening 74 from either side. A dental cast (not shown) is then formed by pouring a settable material, such as wet plaster of Paris, into the mould 18 and allowing it to flow around the sphere 58 and stalk 56, and to set.

In another embodiment of the invention, shown in FIGS. 7 and 8 and described in more detail below, a portion of the plug 54 protrudes into the cavity 19 depending upon the thickness of the plug 54, so that the portion of the plug also becomes embedded in the plaster of Paris.

After setting, the cast, in which the connecting member 16 is embedded, is removed from the mould by deforming the sides and floor of the mould, the connecting member 16 being withdrawn inwardly through the opening 74 as the cast is removed from the mould 18. The spigot 36 of the connector 14 is then inserted into the cavity 33 of the socket 32 of the hinge 12. This process is repeated with a second mould 18.

The dental casts are then aligned in a desired orientation determined by the patient's registered bite. The sphere 58 of the connecting member 16 is placed in the socket 38 of the connector 14. Once the desired orientation of the casts has been obtained, a quick setting adhesive such as a cyanoacrylate adhesive is applied into the slits 50 where it quickly spreads to cover the outer surfaces of the bifurcated sphere 58, and the inner surfaces of the cavity 48 of the socket 38, before setting and immobilising the sphere 58 in the socket 38, and thus holding the casts in the desired orientation. At the same time, the cross-sectional profile of the spigot 36 and the cross-sectional profile of the cavity 33 of the socket 32 prevent rotation of the connector 14 with respect to the hinge 12.

Figure 6:
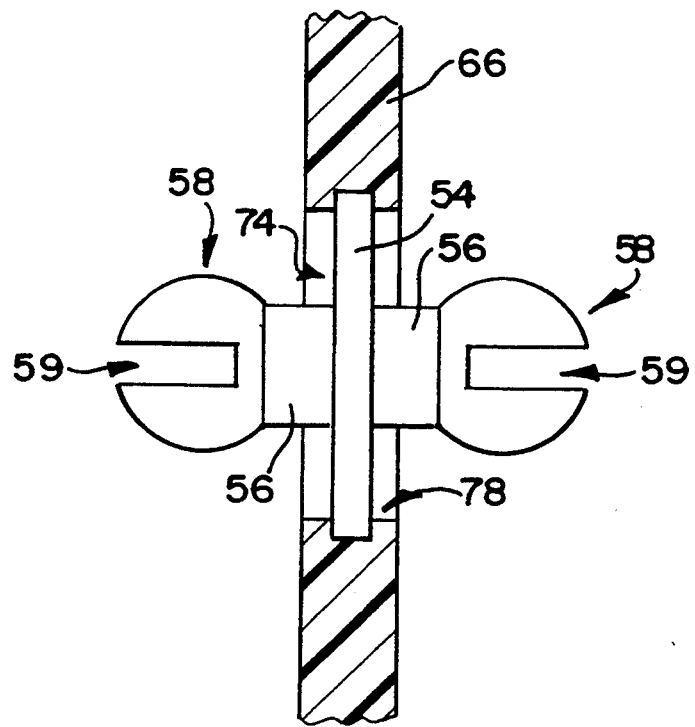
FIG. 6 is a fragmentary plan view, partly in section, on an enlarged scale, of the connecting member shown in FIG. 5 mounted in a mould.
Figure 7:
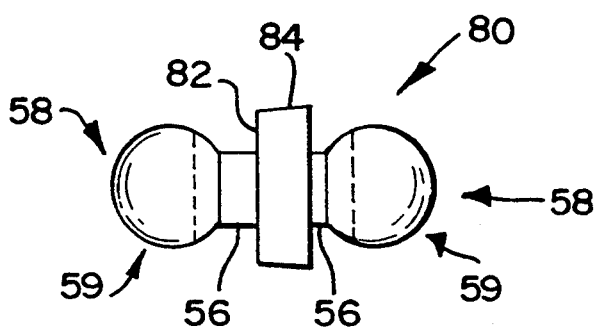
FIG. 7 is a side view of another embodiment of a connecting member of the articulator shown in FIG. 1.

Referring to FIG. 7, another embodiment 80 is shown of a connecting member similar to the connecting member 16 shown in FIGS. 1, 5 and 6. The stalks 56, the spheres 58 and the grooves 59 of the connecting member 80 are the same as for the connecting member 16. The plug 82 is similar to but differs from the plug 54 of the connecting member 16 in that the plug 82 has a tapering peripheral surface 84.

Figure 8:
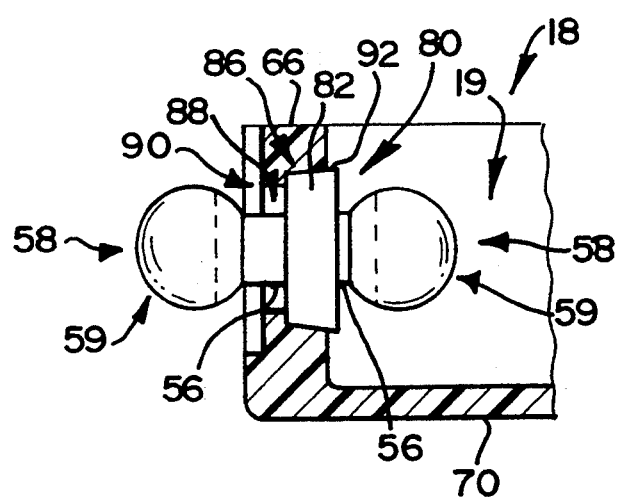
FIG. 8 is a fragmentary side view, partly in section, of the connecting member shown in FIG. 7 mounted in a mould.

Referring to FIG. 8, the connecting member 80 is shown mounted in the base wall 66 of the mould 18 having a floor 70 and a moulding cavity 19 as shown in FIG. 1. A tapering opening 86 complementary to the plug 82 is provided in the wall 66. The opening 86 narrows to an opening 88 which widens into an opening 90 on the outside of the wall 66.

Referring to FIG. 8, in use the connecting member 80 is inserted into the tapering opening 86 so that the plug 82 seats in the opening 86 and one sphere 58 projects into the moulding cavity 19 and the other sphere 58 projects outside the wall 66 through the opening 90. A portion of the plug 82 projects into the moulding cavity 19 to form a ridge 92 diverging into the moulding cavity 19. The ridge 92 forms a gripping surface as will be described below. A dental cast (not shown) is then formed by pouring a settable material, such as wet plaster of Paris, into the mould 18 and allowing it to flow around the sphere 58, the stalk 56 and the ridge 92 on the plug 82, and to set. The tapering ridge 92 forms a gripping surface which enhances the retention of the plug 82 and thus of the connecting member 80 in the dental cast.

Figure 9:
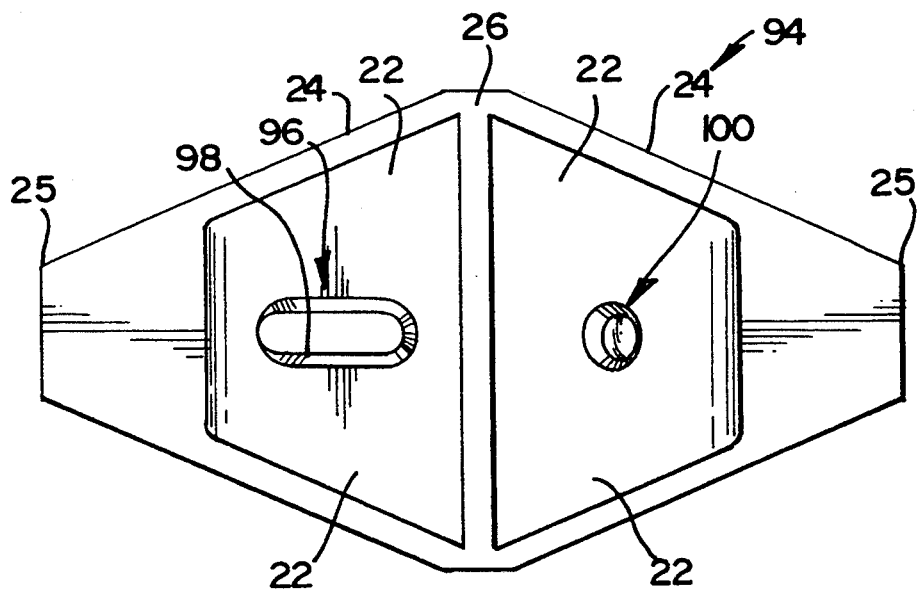
FIG. 9 is a bottom view of another embodiment of a hinge of the articulator shown in FIG. 1.
Figure 10:
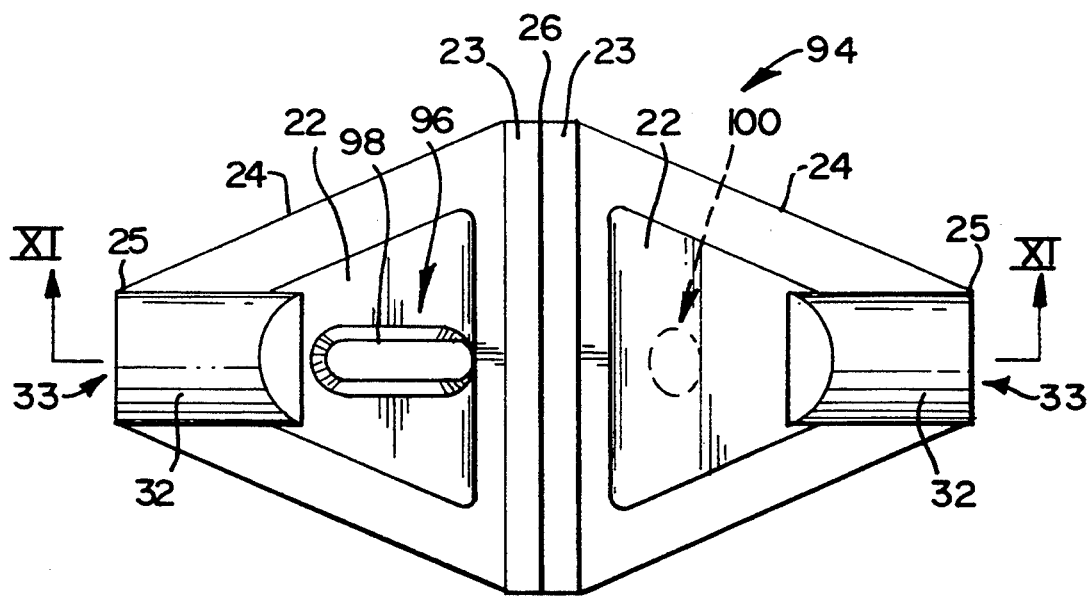
FIG. 10 is a plan view of the hinge shown in FIG. 9.
Figure 11:
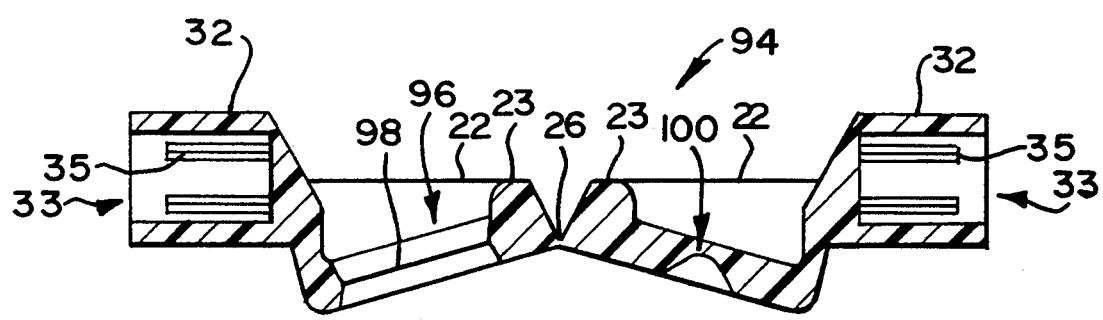
FIG. 11 is a section on line XI—XI of the hinge in FIG. 10.

Referring to FIGS. 9, 10 and 11, there is shown another embodiment 94 of the hinge 12 shown in FIG. 1. The parts 22, 23, 24, 25, 26, 30, 32, 33 and 35 are the same as the like numbered parts of the hinge 12 shown in FIG. 1. The difference is that an elongate slot 96 having a ridge 98 is provided in the one hinge element 22 and a conical recess 100 in the other hinge element 22.

Figure 12:
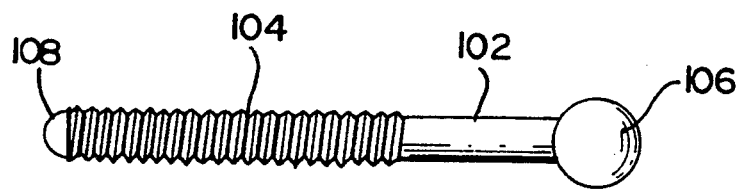
FIG. 12 is a side view of a stay for the hinge shown in FIGS. 9 to 11.
Figure 13:
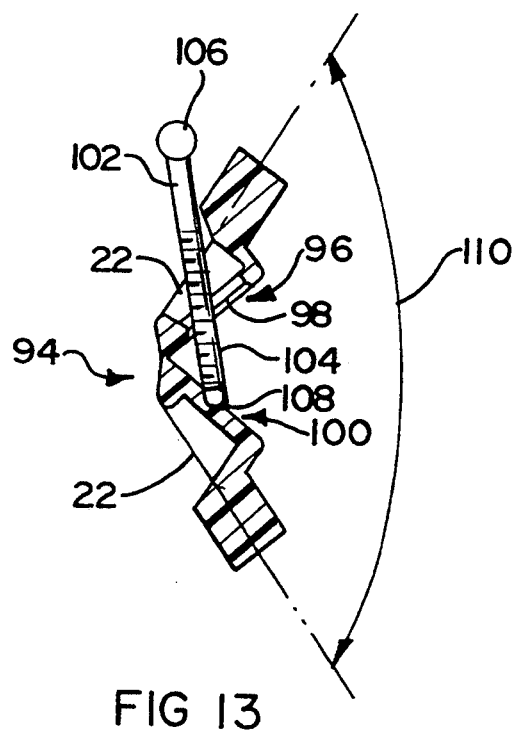
FIG. 13 is a sectional view of the hinge of FIGS. 9 to 11 with the stay of FIG. 12 retaining the hinge in an open position.
Figure 14:
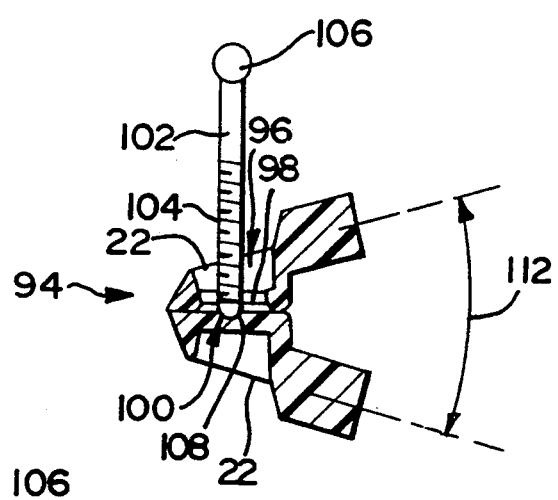
FIG. 14 is a view similar to FIG. 13 but with the hinge in a closed position.

Referring to FIGS. 12, 13 and 14, there is shown a pin 102 having a screw-threaded region 104, a gripping part 106 and a rounded end 108. The pin 102 is screwed onto the ridge 98 to extend through the slot 96 to abut and seat in the recess 100. The pin 102 constitutes a stay for limiting the pivotal displacement of the hinge elements 22 with respect to one another. By screwing the pin 102 onto or out of the ridge 98 in the slot 96 the pivotal displacement of the hinge elements 22 with respect to one another can be limited and adjusted as required. FIG. 13 shows the pin 102 screwed through the slot 96 to such an extent that a fully open position with a maximum angle of displacement 110 between the hinge elements 22 can be effected. FIG. 14 shows the pin 102 screwed through the slot 96 to a limited extent such that a closed position with a minimum angle of 112 between the hinge elements 22 can be effected. The angle 110 may be 110° and the angle 112 may be 30°. Since the rounded end 108 of the pin 102 merely seats in the recess 100 and is not secured in the recess, the angular orientation of the hinge elements with respect to one another is determined by the relevant position of the pin 102 in the slot 96, and can be adjusted by screwingly adjusting the pin. In order to permit the screw threads 104 to engage the ridge 98 from the closed position of the hinge 94 shown in FIG. 14 to the open position of the hinge shown in FIG. 13, the screw threads 104 are not parallel to each other. The screw threads 104 instead are inclined to each other. The angle of inclination of the screw threads 104 to the longitudinal axis of the pin 102 varies from 85° at the end 108 to 50° near the gripping part 106.

Figure 15:
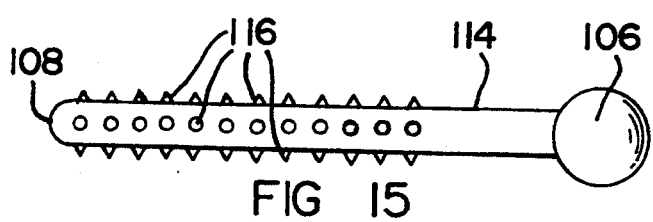
FIG. 15 is a side view of an alternative embodiment of the stay shown in FIG. 12.

Referring to FIG. 15, there is shown an alternative embodiment 114 of the pin 102 shown in FIGS. 12, 13 and 14. The pin 114 also has a gripping part 106 and a rounded end 108. Instead of screw threads 104 the pin 114 has a plurality of nodules 116 arranged in rows and projecting from the pin. The nodules 116 co-operate with the ridge 98 in the slot 96. The pin can be moved into or out of the slot 96 as desired by ratcheting the nodules over the ridge 98 so that the rounded end 108 can seat in the recess 100. The function of the pin 114 is the same as that of the pin 102 as described with reference to FIGS. 12, 13 and 14.

It is an advantage of the invention that the articulator may be assembled before the plaster of the cast is fully dried (this process generally takes a considerable time often requiring extended air-drying or oven drying), as is the case with prior art articulators, where the mounting member is adhesively attached to the cast only after the cast has fully dried.

It is a further advantage of the invention that the cross-shaped cross-sectional profiles of the spigot 36 and cavity 33 of the socket 32 of the connector 14 and hinge 12 respectively prevent rotation of the cast relative to the hinge 12. This is of particular importance, since the dental model is frequently disassembled by removal of the spigot 36 from the cavity 33 when a dental technician is working with the model. The interlocking cross-sectional profiles allow the model to be reassembled without any change or at least with minimal change in the orientation of the dental casts. It is also an advantage of the invention that the bifurcation of the spheres 58 of the mounting member 16 and the slits 50 in the socket 38 of the connector 14 enable rapid penetration and spreading of the adhesive used to secure the connector and mounting member together. Finally, it is an advantage of the invention that the parts of the articulator are of elastically deformable resilient material so that assembling and disassembling the articulator before application of the adhesive is quick and easy to perform.

I claim:

1. An articulator for a dental model comprising two dental casts, the articulator comprising
    a pair of connecting members for partial embedding in a settable material, each connecting member comprising a spigot part of a spigot and socket joint, and each including two spigots of spherical shape and a stalk, each spigot being of a resiliently deformable material and being provided on, and spaced apart by, the stalk and each connecting member including an engagement formation on the stalk between the spigots, the engagement formation comprising a plug of planar shade extending transversely to the stalk and being adapted to plug an opening in a mould for a dental case, each spigot of spherical shape being bifurcated and comprising two hemispheres spaced from one another and defining a groove between them,
    a pair of connectors each comprising a socket part of a spigot and socket joint, and each having an interlocking formation for interlocking engagement with a hinge element, and
    a hinge comprising two hinge elements pivotally linked, each having an interlocking formation complementary to the interlocking formation of the connectors.

2. An articulator as claimed in claim 1, in which the plug has a peripheral surface which tapers in the axial direction of the stalk.

3. An articulator as claimed in claim 1, in which the socket part of the connector is of hemispherical shape and includes at least one slit extending inwardly from its periphery, the socket part being of a resiliently deformable material.

4. An articulator as claimed in claim 1, in which the interlocking formations of the connectors and of the hinge elements are a spigot formation and a complementary socket formation.

5. An articulator as claimed in claim 4, in which the spigot formation has a guide formation and the complementary socket formation has a complementary recessed guide formation, the guide formation of the spigot formation being engageable with the complementary recessed guide formation of the complementary socket formation to prevent rotation of the spigot formation relative to the socket formation.

6. An articulator as claimed in claim 1, in which the hinge elements are connected to one another by a joint of flexible material.

7. An articulator as claimed in claim 6, in which each hinge element defines a generally triangular shape, having three sides, one side being a connected side which is partially linked by the joint of flexible material to the other hinge element, and the other two sides together defining an apex of the triangular shade opposite the connected side, the joint of flexible material extending between, and pivotally linking, each connected side of each triangular shaped hinge element and each interlocking formation being located generally at the apex of the triangular shape defined by each hinge element opposite each connected side of each hinge element.

8. An articulator as claimed in claim 1, in which the hinge and the connectors are of different synthetic plastic materials so that an adhesive will not readily form a bond between them.

9. An articulator as claimed in claim 1, in which the hinge includes a stay to limit pivotal movement of the hinge elements with respect to one another.

10. An articulator as claimed in claim 9, in which one of the hinge elements is provided with a hole, and the stay comprises a pin having restraining formations, and which pin can be displaced into the hole and which pin can abut the other of said hinge elements, the restraining formations engaging the edge of the hinge element defining the hole to locate the pin in the hole, the pin thereby limiting the pivotal movement of the hinge elements with respect to one another.

11. An articulator as claimed in claim 10, in which the hole is elongate and has a ridge with which the restraining formations of the pin can co-operate.

12. An articulator as claimed in claim 10, in which the restraining formations are screw threads.

13. An articulator as claimed in claim 16, in which the restraining formations are nodules.

14. A dental articulator kit which includes a dental articulator comprising a pair of connecting members for partial embedding in a settable material, each connecting member comprising a spigot part of a spigot and socket joint, and each including two spigots of spherical shape and a stalk, each spigot being of a resiliently deformable material and being provided on, and spaced apart by, the stalk and each connecting member including an engagement formation on the stalk between the spigots, the engagement formation comprising a plug of planar shape extending transversely to the stalk and being adapted to plug an opening in a mould for a dental cast, each spigot of spherical shape being bifurcated and comprising two hemispheres spaced from one another and defining a groove between them, a pair of connectors each comprising a socket part of a spigot and socket joint, and each having an interlocking formation for interlocking engagement with a hinge element, and a hinge comprising two hinge elements pivotally linked, each element having an interlocking formation complementary to the interlocking formation of the connectors, and a mould defining a moulding cavity for receiving a settable material for making a dental cast for use with the dental articulator, the mould being substantially triangular in shape, simulating the shape of a person's jaw and being open having a floor and side walls defining the moulding cavity into which the settable material may be poured, and being provided with an opening for receiving the engagement formation.

15. A method of assembling a dental articulator, the method including the steps of locating a connecting member in an opening in a mould defining a moulding cavity for a dental cast so that a portion of the connecting member projects from the mould and a portion projects through said opening into the moulding cavity;

pouring a settable material into the mould and allowing the settable material to flow around the portion of the connecting member projecting into the moulding cavity and to set thereby forming a dental cast with the connecting member embedded in and projecting from the cast;

attaching a pair of connectors to the connecting member; and attaching a hinge to the pair of connectors thereby to assemble the dental cast.

* * * * *